US00PP25678P2

(12) United States Plant Patent
Lannes

(10) Patent No.: US PP25,678 P2
(45) Date of Patent: Jul. 7, 2015

(54) ***HIBISCUS* PLANT NAMED 'LANRED'**

(50) Latin Name: *Hibiscus rosa-sinensis*
Varietal Denomination: Lanred

(71) Applicant: Robert Lannes, Malause (FR)

(72) Inventor: Robert Lannes, Malause (FR)

( * ) Notice: Subject to any disclaimer, the term of this patent is extended or adjusted under 35 U.S.C. 154(b) by 176 days.

(21) Appl. No.: 13/987,545

(22) Filed: Aug. 6, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — June Hwu
(74) *Attorney, Agent, or Firm* — Penny J. Aguirre

(57) ABSTRACT

A new cultivar of *Hibiscus* named 'Lanred', that is characterized by its large flowers that are round in shape and bright red with a dark red eye zone, its short leaf internode lengths, its very dark green foliage, its good self-branching, its vigorous growth habit, and its early blooming habit.

2 Drawing Sheets

Botanical classification: *Hibiscus rosa-sinensis*.
Cultivar designation: 'Lanred'.

BACKGROUND OF THE INVENTION

The present invention relates to a new and distinct cultivar of *Hibiscus* plant of hybrid origin, botanically known as *Hibiscus rosa-sinensis* 'Lanred' and will be referred to hereafter by its cultivar name, 'Lanred'. 'Lanred' is a new cultivar of tropical *Hibiscus* grown for use as a landscape and container plant.

The new cultivar was developed through an on-going breeding program conducted by the Inventor in Malause, France. The objectives of the breeding program are to develop new cultivars of *Hibiscus* that exhibit compact plant habits with self-branching and a well-balanced plant habit.

The Inventor made a cross in July of 2006 between 'Nelly Rose Clair' (not patented) as the female parent and 'Vatican Rouge' (not patented) as the male parent. 'Lanred' was selected as a single unique plant from the resulting seedlings in September of 2009.

Asexual propagation of the new cultivar was first accomplished by stem cuttings in Malause, France in September of 2009 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'Lanred'. These attributes in combination distinguish 'Lanred' as a new and distinct cultivar of *Hibiscus*.

1. 'Lanred' exhibits large flowers that are round in shape and bright red with a dark red eye zone.
2. 'Lanred' exhibits short leaf internode lengths.
3. 'Lanred' exhibits very dark green foliage.
4. 'Lanred' exhibits good self-branching.
5. 'Lanred' exhibits a vigorous growth habit.
6. 'Lanred' commences bloom early in summer.

The female parent of 'Lanred', 'Nelly Rose Clair', differs from 'Lanred' in having smaller flowers that are pink in color and in having less self-branching. The male parent of 'Lanred', 'Vatican Rouge', differs from 'Lanred' in having flowers that are darker red in color and in having less self-branching. 'Lanred' can also be most closely compared to the cultivars 'Grandiflora Red' (not patented) and 'Alicante' (not patented). Both are similar to 'Lanred' in having flowers that are red in color. 'Grandiflora Red' differs from 'Lanred' in having flowers that lack a dark center eye zone, in commencing bloom later in the season, in having less self-branching and in having longer leaf internodes. 'Alicante' differs from 'Lanred' in having flowers that are smaller, and in commencing bloom later in the season.

BRIEF DESCRIPTION OF THE DRAWING

The accompanying colored photograph illustrates the overall appearance and distinct characteristics of the new *Hibiscus*. The photographs were taken of a six month-old plant of 'Lanred' as grown in a one-gallon container in a greenhouse in Malause, France.

The photograph in FIG. 1 provides a side view of 'Lanred' in bloom.

Figure 1:
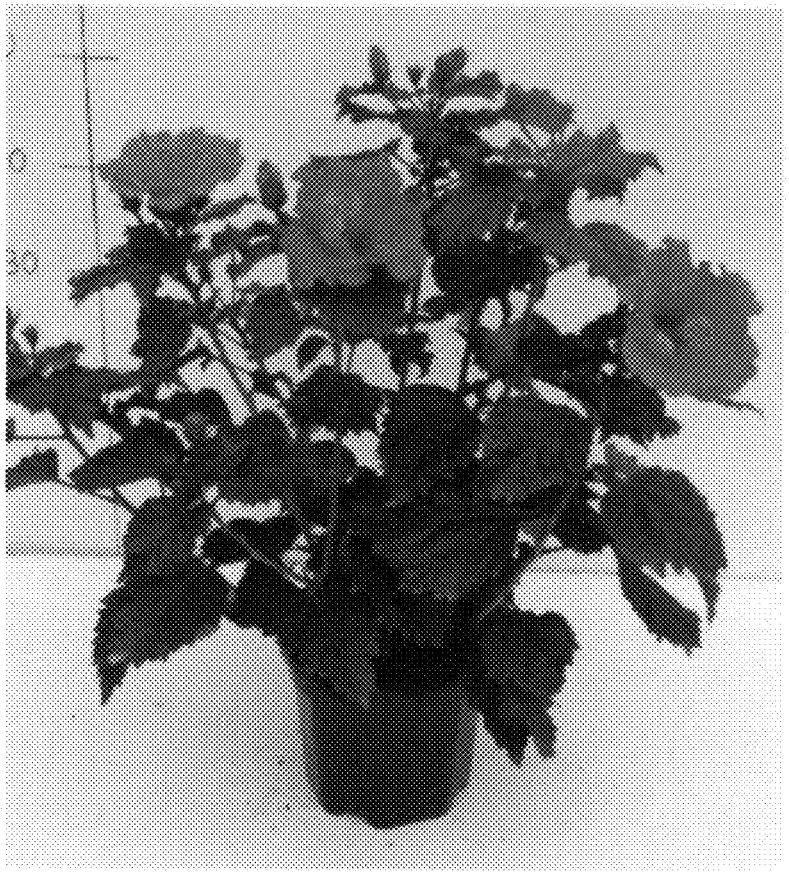
Figure 2:
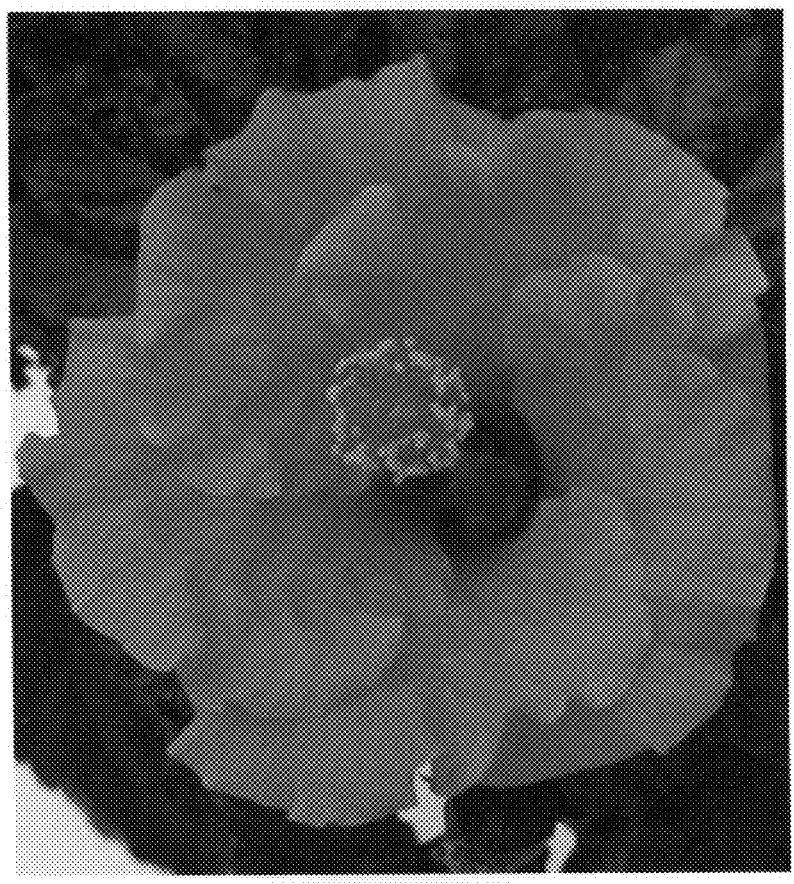

The photograph in FIG. 2 provides a close-up view of a flower of 'Lamed'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 6 month-old plants of the new cultivar as grown in two-quart containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Commences bloom in early summer and blooms continuously throughout the summer in Grand Saline, Tex. and Malause, France.

*Plant type*.—Tropical evergreen shrub.

*Plant habit*.—Upright and slightly spreading, compact.

*Height and spread*.—Reaches 45 to 55 cm in height and 35 to 45 cm in spread.

*Hardiness*.—At least in U.S.D.A. Zones 9 to 11.

*Diseases*.—No susceptibility or resistance to diseases has been observed.

*Root description*.—Fibrous roots.

*Propagation*.—Stem cutting.

*Growth rate*.—Vigorous.

Stem description:

*Shape*.—Slightly oval.

*Stem color*.—New growth; 138A, mature wood; 156A.

*Stem size*.—Main stems; an average of 12.5 cm in length and 4 mm in width.

*Stem surface*.—New growth; very sparse hairs, bark; very finely striated with small lenticels.

*Stem aspect*.—Held upright to an average angle of 5° (0°=vertical).

*Stem strength*.—Strong.

*Branching*.—Self-branching, an average of 2 main stems and 2 lateral branches per main stem in a two-quart container.

*Internode*.—Average of 1.8 cm

Foliage description:

*Leaf shape*.—Ovate.

*Leaf division*.—Simple.

*Leaf base*.—Rounded.

*Leaf apex*.—Acute.

*Leaf venation*.—Pinnate, 138A in color in upper and lower surface.

*Leaf margins*.—Serrate.

*Leaf attachment*.—Petiolate.

*Leaf arrangement*.—Alternate.

*Leaf orientation*.—Held horizontal to slightly downward.

*Leaf aspect*.—Slightly cupped outward to flat.

*Leaf surface*.—Upper surface glabrous and glossy, lower surface very sparsely pubescent and satiny.

*Leaf color*.—Young leaves upper and lower surface; 137B , mature leaves upper surface; 139A, mature leaves lower surface; 138A.

*Leaf size*.—Average of 7.6 cm in length, and 6.0 cm in width.

*Leaf quantity*.—About 6 leaves per main branch 12.5 cm in length.

*Petioles*.—Average of 3.0 cm in length and 2.0 mm in diameter, 138A in color, pubescent surface.

Flower description:

*Inflorescence type*.—Flowers are solitary.

*Lastingness of flowers*.—1 to 2 days, self cleaning.

*Flower size*.—An average of 7 cm in depth (including reproductive organs) and 10 cm in diameter.

*Flower fragrance*.—None.

*Flower shape*.—Rotate, rounded with overlapping petals.

*Flower number*.—Average of 5 per lateral stem.

*Flower aspect*.—Slightly outward from horizontal.

*Flower bud*.—Oblong in shape, an average of 3 cm in length and 1.5 cm in width and N34 in color.

*Flower attachment*.—Attached to peduncle.

*Petal number*.—5.

*Petal shape*.—Rounded.

*Petal color*.—Upper surface when opening and mature; 43A with eye zone 53A, lower surface when opening and mature 43A, fades to a blend of 43A and 43B on upper surface with eye zone 53A and a blend of 43A and 43B on lower surface.

*Petal surface*.—Upper surface smooth with base of petals (eye zone) highly glossy.

*Petal margins*.—Slightly crenate and wavy.

*Petal apex*.—Rounded.

*Petal base*.—Broadly cuneate and adnate to base of stamen tube.

*Petal size*.—Average of 5.5 cm in length and width.

*Petal aspect*.—Slightly upward from horizontal.

*Sepal number*.—5.

*Sepal shape*.—Elliptic.

*Sepal margin*.—Entire.

*Sepal size*.—Average of 2.5 cm in length and 1 cm in width.

*Sepal aspect*.—Upright, lower 50% fused.

*Sepal surface*.—Upper (outer) surface slightly rough to the touch and dull, lower surface (inner) smooth and glossy.

*Sepal apex*.—Acute.

*Sepal base*.—Fused.

*Sepal color*.—Young and mature upper (outer) surface; 137C, lower (inner) surface; a blend of 144A and 144B.

*Calyx*.—Campanulate in shape, average of 2.5 cm in length and 1.7 cm in diameter.

*Peduncles*.—An average of 7.7 cm in length (including a 2 cm segment towards base of flower that is wider and separated by a ligule) and 3 mm in diameter, strong, average angle is 35° (0°=straight on top of lateral branch) and 144A in color with ligule 137B, very slightly pubescent surface.

*Pedicels*.—Not present, flowers are solitary from terminal leaf axils.

*Bracts*.—Average of 7 bracts held upright surrounding sepals, lanceolate in shape, average of 1.8 cm in length and 3 mm in width, a blend of 137B and 137C in color on inner and outer surface, surface is slightly pubescent on inner and outer surface.

Reproductive organs:

*Gynoecium*.—1 pistil, about 42 cm in length and 3 to 5 mm in width, stigmas; club-shaped and an average of 5, 43A in color, style; 3.9 cm in length and 45B in color, ovary; cone-shaped, about 1 cm in length and 6 mm in width, 1B in color but completely covered by the base of the pistil style.

*Androecium*.—Stamens; average of 80, stamens are clustered and implanted in style, anthers; dorsifixed and orbicular in shape, 1.5 mm in length and 2 mm in width, and 160D in color; filament; 2 mm in length, 4 mm in width, and 43A in color, pollen; abundant in quantity and 17A in color.

*Fruit/seeds*.—None observed.

It is claimed:

1. A new and distinct cultivar of *Hibiscus* plant named 'Lanred' as herein illustrated and described.

* * * * *